(12) United States Patent
Sherman

(10) Patent No.: US 6,767,556 B2
(45) Date of Patent: Jul. 27, 2004

(54) PHARMACEUTICAL COMPOSITIONS COMPRISING MOEXIPRIL MAGNESIUM

(75) Inventor: Bernard Charles Sherman, 50 Old Colony Road, Willowdale (CA), M2L 2K1

(73) Assignee: Bernard Charles Sherman, Toronto (CA)

( * ) Notice: Subject to any disclaimer, the term of this patent is extended or adjusted under 35 U.S.C. 154(b) by 0 days.

(21) Appl. No.: 09/809,173

(22) Filed: Mar. 16, 2001

(65) Prior Publication Data

US 2002/0037858 A1 Mar. 28, 2002

(30) Foreign Application Priority Data

Apr. 5, 2000 (CA) .............................................. 2303481

(51) Int. Cl.$^7$ ............................. A61K 9/14; A61K 9/48; A61K 9/64; A61K 9/20
(52) U.S. Cl. ...................... 424/489; 424/451; 424/452; 424/456; 424/464; 424/465
(58) Field of Search ................................ 424/489, 464, 424/465, 451, 452, 456

(56) References Cited

U.S. PATENT DOCUMENTS 4,344,949 A * 8/1982 Hoefle et al. ................ 424/258
4,743,450 A * 5/1988 Harris et al. ................. 424/440

OTHER PUBLICATIONS

Drug–Excipient Incompatibility Studies of the Dipeptide Angiotensin–Converting Enzyme Inhibitor, Moexipril Hydrochloride: Dry Powder vs. Wet Granulation (Gu et al., Pharmaceutical Research, vol. 7, No. 4, 1990, pp. 379–383).*
Results from FDA Orange Book for Exclusivity Data with respect to UNIVASC.
Product for Monograph for UNIVASC.

* cited by examiner

Primary Examiner—Thurman K. Page
Assistant Examiner—Humera N. Sheikh
(74) Attorney, Agent, or Firm—Neil H. Hughes; Ivor M. Hughes; Marcelo Sarkis

(57) ABSTRACT

Stable solid compositions comprising moxeipril magnesium can be made using moexipril or an acid addition salt thereof, by reacting the moexipril or acid addition salt with an alkaline magnesium compound in the presence of a solvent, so as to convert most or all of the moexipril or acid addition salt to moexipril magnesium.

15 Claims, No Drawings

PHARMACEUTICAL COMPOSITIONS COMPRISING MOEXIPRIL MAGNESIUM

FIELD OF INVENTION

This invention relates to solid pharmaceutical compositions comprising a stable salt of moexipril, specifically the magnesium salt, moexipril magnesium.

BACKGROUND

Some ACE (Angiotensin Converting Enzyme) inhibitors, which are useful as antihypertensives, are susceptible to degradation by cyclization, hydrolysis or oxidation. Such ACE inhibitors include enalapril, quinapril and moexipril, and acid addition salts thereof.

Enalapril and its acid addition salts and their use as ACE inhibitors, is disclosed in U.S. Pat. No. 4,374,829.

Quinapril and moexipril and their acid addition salts are disclosed in U.S. Pat. No. 4,344,949.

Various methods of improving the stability of these compounds are disclosed in the prior art.

Enalapril and its acid addition salts are more easily stabilized than moexipril and its acid addition salts. There are thus some methods in the prior art that are satisfactory for the stabilization of enalapril and its acid addition salts, but not moexipril and its acid addition salts.

U.S. Pat. No. 5,562,921 discloses that stable tablets can be made comprising enalapril maleate by restricting the inactive ingredients used in the tablets to certain ones found not to cause degradation. However, because moexipril and its acid addition salts are less stable than enalapril maleate, this approach does not work with moexipril and its acid addition salts.

U.S. Pat. Nos. 5,350,582 and 5,573,780 both disclose that stable tablets can be made by reacting enalapril maleate with an alkaline sodium compound to convert the enalapril maleate to enalapril sodium. Enalapril sodium is found to be much more stable than enalapril maleate.

U.S. Pat. No. 4,830,853 discloses that certain ACE inhibitors, and in particular quinapril, can be stabilized against oxidation and discoloration by including ascorbic acid or sodium ascorbate in the composition. However, it appears that this approach does not stabilize moexipril or its addition salts sufficiently to be commercially useful, as products presently being marketed do not use this approach.

Finally, U.S. Pat. No. 4,743,450 discloses that certain ACE inhibitors can be stabilized by making solid compositions that include an alkaline compound as stabilizer. Magnesium, calcium and sodium compounds are said to be preferred, and magnesium is most preferred. The examples in this patent all relate to solid dosage forms comprising quinapril hydrochloride as active drug and magnesium carbonate as stabilizer.

There is also a relevant publication by Gu et al, "Drug-Excipient Incompatibility Studies of the Dipeptide Angiotensin Converting Enzyme Inhibitor, Moexipril Hydrochloride: Dry Powder vs Wet Granulation", Pharm Res. 7(4): 370–383. This publication discloses that moexipril hydrochloride can be stabilized by making compositions comprising moexipril hydrochloride and an alkaline stabilizing agent selected from sodium bicarbonate, sodium carbonate and calcium carbonate. It is stated that the stabilization is accomplished only when the compositions are made by a wet granulation process. In the conclusion of the publication, it is postulated that the stabilization results from the neutralization of the acidic drug by the basic excipient at the outer surface of the granulated material. It is also stated that it is possible that a portion of the moexipril was converted to alkaline salts via granulation. It thus appears clear that Gu, et al teaches that only a portion (if any) of the drug, and only that portion at the outer surface of the granules, may be converted to the alkaline salt, and that the stable product thus results entirely or primarily not from conversion to alkaline salts, but from stabilization of the moexipril hydrochloride by the presence of the alkaline stabilizing compound in the final product.

Gu, et al is thus consistent with the teaching of U.S. Pat. No. 4,743,450, which, as aforesaid, teaches stable compositions comprising the unstable drug, stabilized by the presence of an alkaline compound in the final composition.

Tablets containing moexipril hydrochloride are sold in the United States and elsewhere under the tradename Univasc® by Schwarz Pharma. The labeling of these tablets indicates that the tablets contain moexipril hydrochloride and magnesium oxide. This indicates that these tablets are compositions in accordance with the teaching of U.S. Pat. No. 4,743,450.

There are certain problems inherent in the teaching of U.S. Pat. No. 4,743,450. In particular:

1. The examples of U.S. Pat. No. 4,743,450 indicate a ratio of magnesium carbonate to active drug from about 5.8 to about 16.5 by weight, so that it appears that the amount of magnesium compound required is large and substantially exceeds the amount of the active drug.
2. Using the approach of U.S. Pat. No. 4,743,450, it is difficult to precisely control the exact final ingredients in the composition. The moexipril hydrochloride and magnesium compound are capable of an acid-base reaction. It is difficult to control the process so as to completely avoid an acid-base reaction in the making of the composition. The exact composition of the final product is thus uncertain and probably variable, if the teaching of U.S. Pat. No. 4,743,450 is followed.

In light of the prior art, the object of the present invention is to enable a stable composition comprising a moexipril salt which overcomes these limitations of the prior art.

DESCRIPTION OF THE INVENTION

Improved stability is achieved by producing a dosage form which comprises moexipril magnesium.

It has been found that the magnesium salt of moexipril (i.e. moexipril magnesium) is sufficiently stable to enable stable solid compositions, without the presence of an alkaline stabilizing compound in the final composition. It has also been found that stable solid compositions comprising moexipril magnesium can be made using moexipril or an acid addition salt thereof, by reacting the moexipril or acid addition salt with an alkaline magnesium compound, so as to convert most or all (i.e. more than half) of the moexipril or acid addition salt to moexipril magnesium.

Since the purpose of the present invention is to eliminate the unstable moexipril or acid addition salt thereof and replace it with stable moexipril magnesium, it will be understood that it is desirable that the preparation of the moexipril or acid addition salt converted and moexipril magnesium be as high as possible. Hence the amount converted will preferably be more than 70%, more preferably more than 80%, even more preferably more than 90%, and most preferably 100% or virtually 100%.

The moexipril or acid addition salt thereof used in the process will preferably be moexipril hydrochloride.

The alkaline magnesium compound will preferably be magnesium hydroxide or the magnesium salt of a weak acid such as, for example, magnesium carbonate. Magnesium oxide may be used in place of magnesium hydroxide, as magnesium oxide will convert to magnesium hydroxide in the presence of water.

The molecular formula for moexipril hydrochloride is $C_{27}H_{34}N_2O_7 \cdot HCl$ and the molecular weight is 535.04 g.

The molecular equations, for converting moexipril hydrochloride to moexipril magnesium plus magnesium chloride, by reacting with magnesium hydroxide and magnesium carbonate are as follows:

1) Using magnesium hydroxide:

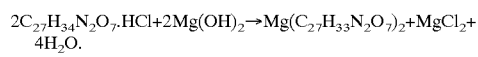

$$2C_{27}H_{34}N_2O_7 \cdot HCl + 2Mg(OH)_2 \rightarrow Mg(C_{27}H_{33}N_2O_7)_2 + MgCl_2 + 4H_2O.$$

2) Using magnesium carbonate:

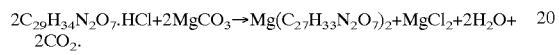

$$2C_{29}H_{34}N_2O_7 \cdot HCl + 2MgCO_3 \rightarrow Mg(C_{27}H_{33}N_2O_7)_2 + MgCl_2 + 2H_2O + 2CO_2.$$

It can be seen that a complete conversion of moexipril hydrochloride to moexipril magnesium plus magnesium chloride requires for each mole (535 g) of moexipril hydrochloride, the following minimum amount of alkaline magnesium compound:

i) If magnesium hydroxide is used, one mole, which is 58.3 g.

ii) If magnesium carbonate is used, one mole, which is 84.3 g.

If only the minimum amount of alkaline magnesium compound, so calculated, is used, it is possible that the reaction may not go to completion, leaving some of the moexipril or acid addition salt not converted to moexipril magnesium. It is thus preferable to use an excess amount of alkaline magnesium compound, to help ensure the reaction is complete or substantially complete.

A reaction to convert the moexipril or acid addition salt thereof to moexipril magnesium cannot be accomplished simply by mixing the moexipril or acid addition salt together with the alkaline magnesium compound in dry form. It is necessary to mix and react the moexipril or acid addition salt and the alkaline magnesium compound with the aid of solvent, which may be water or organic solvent or a mixture of water and organic solvent, and then evaporating the solvent to obtain a dry substance. The solvent will preferably be a mixture of water and organic solvent, and a preferred organic solvent is acetone. After the solvent is evaporated, the dried material obtained will be further processed into a dosage form, such as a tablet or capsule.

This process may be carried out in any of several ways, as follows:

i) The moexipril or acid addition salt and the alkaline magnesium compound can be reacted by adding them to solvent and mixing in the liquid state until the reaction is complete. As aforesaid, the solvent may be water or organic solvent, or a mixture of water and one or more organic solvents. The solvent will preferably be a mixture of water and an organic solvent, and most preferably a mixture of water and acetone. The amount of solvent will preferably be sufficient to fully dissolve the resultant moexipril magnesium, but not necessarily the excess alkaline magnesium compound, assuming an excess was used. After the reaction is completed, it is necessary to evaporate the solvent. This can be done, for example, by filtering the liquid to remove the extra alkaline magnesium compound, if any, and then spray drying. The resulting dry powder will be a mixture of moexipril magnesium and the magnesium salt of the acid used in the moexipril acid addition salt (i.e. magnesium chloride if moexipril hydrochloride was used). This dry powder can then be mixed with other suitable excipients (i.e. inactive ingredients such as, for example, lactose), and that mixture can be further processed into solid compositions; i.e. compressed into tablets or used as fill for two-piece hard gelatin capsules.

ii) The moexipril or acid addition salt and the alkaline magnesium compound can be reacted in a liquid state as described in i) above. However, instead of then evaporating the solvent, the resultant liquid or suspension can be used to wet granulate other excipients, and the wet mass can then be dried, for example, in an oven or fluid bed drier. The dried mass can then be compressed into tablets or used as fill for capsules, with or without the addition of other excipients.

iii) The moexipril or acid addition salt can be mixed with one or more excipients, for example lactose, in a dry state, and then the dry mixture can be wet granulated with a solution or suspension of the alkaline magnesium compound in suitable solvent, thereby forming a wet mass. A sufficient quantity of suitable solvent must be used and the mass must be left wet enough for sufficient time to enable the reaction between the moexipril or acid addition salt and the alkaline magnesium compound to be complete or substantially complete, before the solvent is removed by drying the wet mass. The wet mass is then dried, and the dried material can then be compressed into tablets or used as a fill for capsules, with or without the addition of other excipients.

iv) The magnesium compound can be mixed with other excipients, for example lactose, in a dry state, and then the dry mixture can be wet granulated with a solution or suspension of the moexipril or acid addition salt in suitable solvent, thereby forming a wet mass. Again, a sufficient quantity of suitable solvent must be used and the mass must be left wet enough for sufficient time to enable the reaction between the moexipril or acid addition salt and the alkaline magnesium compound to be complete or substantially complete, before the solvent is removed by drying the wet mass. The wet mass is then dried, and the dried material can then be compressed into tablets or used as a fill for capsules, with or without the addition of other excipients.

v) The moexipril or acid addition salt thereof and the alkaline magnesium compound can both be mixed with other excipients, for example lactose, in a dry state and then the dry mixture can be wet granulated with solvent to form a wet mass. Again, a sufficient quantity of suitable solvent must be used and the mass must be left wet enough for sufficient time to enable the reaction between the moexipril or acid addition salt and the alkaline magnesium compound to be complete or substantially complete, before the solvent is removed by drying. The wet mass is then dried, and the dried material can then be compressed into tablets or used as a fill for capsules, with or without the addition of other excipients.

The invention will be further understood from the following examples which are intended to be illustrative but not limiting of the invention.

EXAMPLE 1

The following ingredients were mixed together for 30 minutes:

| | |
|---|---:|
| Moexipril hydrochloride | 10.0 g |
| Magnesium hydroxide | 10.0 g |
| Povidone | 30.0 g |
| Water | 480.0 g |
| Acetone | 240.0 g |
| Total | 770.0 g |

In the liquid mixture, the 10.0 g of moexipril hydrochloride reacted with 1.09 g of magnesium hydroxide to produce 9.53 g of moexipril magnesium plus 0.89 g of magnesium chloride, plus 0.67 g of water. The liquid was then filtered to remove the excess magnesium hydroxide.

Hence the material dissolved in the water and acetone after filtration was:

| | |
|---|---:|
| Moexipril magnesium | 9.53 g |
| Magnesium chloride | 0.89 g |
| Povidone | 30.00 g |
| Total | 40.42 g |

The spray-dried powder thus contained moexipril magnesium at a concentration of 9.53 g of per 40.42 g. Because of the relative molecular weights of moexipril magnesium versus moexipril, 9.53 g of moexipril magnesium is equivalent in activity to 9.32 g of moexipril. Hence the potency of the spray-dried powder expressed as moexipril equivalent was 9.32 g per 39.19 g.

A portion of the spray-dried powder was mixed with other ingredients as follows:

| | |
|---|---:|
| Spray-dried powder | 11.0 g |
| Lactose monohydrate | 13.0 g |
| Magnesium stearate | 0.25 g |
| Red ferric oxide | 0.7 g |
| Colloidal silicon dioxide | 0.05 g |
| Total | 25.0 g |

This mixture was compressed into tablets of weight 50 mg each. Each tablet thus contained 22 mg of the spray-dried powder, which in turn contained about 5.2 mg of moexipril magnesium, equivalent to about 5.1 mg of moexipril.

EXAMPLES 2 TO 4

Ingredients were used as follows:

| | Example 2 | Example 3 | Example 4 |
|---|---:|---:|---:|
| Moexipril Hydrochloride | 5.4 g | 5.4 g | 5.4 g |
| Magnesium Hydroxide | 5.4 g | 5.4 g | 5.4 g |
| Lactose anhydrous | 37.2 g | 37.2 g | 37.2 g |
| Water | 12.0 g | 6.0 g | 0 g |
| Acetone | 0 g | 6.0 g | 12.0 g |
| Total | 60.0 g | 60.0 g | 60.0 g |
| Total excluding solvent | 48.0 g | 48.0 g | 48.0 g |

The procedure followed was to mix the first three ingredients together, and then add the solvent (i.e. water and/or acetone as shown) and mix well again. The wet mass was allowed to sit wet for 30 minutes and then mixed again before drying, to ensure that the mixture was wet enough for long enough to allow to reaction between the moexipril hydrochloride and magnesium hydroxide to go to completion or substantial completion. The wet mass was then dried in an oven at 60° C. for four hours and the dried material was then passed through a #20 screen to produce fine granules.

For the resulting fine granules of each of these examples, 1.0 g of magnesium stearate was mixed with 24 g of the granules, and this mixture was compressed into tablets of 50 mg weight each. Because of the relative amounts of the various ingredients used and the relative molecular weights, it follows that each tablet of each of examples 2, 3 and 4 contained about 5.1 mg of moexipril magnesium equivalent to about 5.0 mg of moexipril.

The tablets of examples 1, 2, 3 and 4 are more stable against degradation of the active drug than tablets comprising moexipril hydrochloride which has neither been converted to moexipril magnesium nor stabilized by addition of a stabilizer.

The embodiments of the invention in which an exclusive property or privilege is claimed are as follows:

1. A process of making a solid pharmaceutical composition comprising moexipril magnesium, said process comprising the step of reacting moexipril or an acid addition salt thereof with an alkaline magnesium compound in a controlled manner in the presence of a sufficient amount of solvent for a predetermined amount of time so as to convert greater then 80% of the moexipril or moexipril acid addition salt to moexipril magnesium.

2. The process of claim 1 comprising the steps of:
   i) adding the moexipril or acid addition salt thereof and the alkaline magnesium compound to solvent and mixing in the liquid state;
   ii) evaporating the solvent to obtain a dried material, and
   iii) further processing the dried material into the solid pharmaceutical composition.

3. The process of claim 2 wherein, before the solvent is evaporated, the liquid is filtered to remove unreacted alkaline magnesium compound.

4. The process of claim 2 or 3 wherein the solvent is evaporated by spray-drying.

5. The process of claim 1 comprising the steps of:
   i) adding the moexipril or acid addition salt thereof and the alkaline magnesium compound to solvent;
   ii) using the resultant solution or suspension to wet granulate with excipients to obtain a wet mass;
   iii) drying the wet mass to obtain a dried mass; and
   iv) further processing the dried mass into the solid pharmaceutical composition.

6. The process of claim 1 comprising the steps of:
   i) adding the alkaline magnesium compound to solvent;
   ii) using the resulting solution or suspension to wet granulate a mixture of the moexipril or acid addition salt thereof and one or more excipients to obtain a wet mass;
   iii) drying the wet mass to obtain a dried mass; and
   iv) further processing the dried mass into the solid pharmaceutical composition.

7. The process of claim 1 comprising the steps of:
   i) adding the moexipril or acid addition salt thereof to solvent;
   ii) using the resultant solution or suspension to wet granulate a mixture of the alkaline magnesium compound and one or more excipients to obtain wet mass;

iii) drying the wet mass to obtain a dried mass, and iv) further processing the dried mass into the solid pharmaceutical composition.

8. The process of claim 1 comprising the steps of:

i) mixing the moexipril or acid addition salt thereof and alkaline magnesium compound with one or more excipients;

ii) adding a solvent and mixing to obtain a wet mass;

iii) drying the wet mass to obtain a dry mass; and iv) further processing the dried mass into the solid pharmaceutical composition.

9. The process of any one of claims 1, 2, 3, 5, 6, 7, or 8 where the solvent is selected from a group of solvents comprising water, an organic solvent, acetone, or combinations thereof.

10. The process of any one of claims 1, 2, 3, 5, 6, 7, or 8 wherein the moexipril or acid addition salt thereof is moexipril hydrochloride.

11. The process of any one of claims 1, 2, 3, 5, 6, 7, or 8 wherein the alkaline magnesium compound is selected from the group of compounds comprising magnesium hydroxide, magnesium oxide, magnesium carbonate, or the magnesium salt of a weak acid.

12. The process of any one of claims 1, 2, 3, 5, 6, 7, or 8 wherein the percentage of the moexipril or acid addition salt converted to moexipril magnesium is greater than 90%.

13. The process of claim 4 where the solvent is selected from a group of solvents comprising water, an organic solvent, acetone, or combinations thereof.

14. The process of claim 4 wherein the moexipril or acid addition salt thereof is moexipril hydrochloride.

15. The process of claim 4 wherein the alkaline magnesium compound is selected from the group of compounds comprising magnesium hydroxide, magnesium oxide, magnesium carbonate, or the magnesium salt of a weak acid.

* * * * *